United States Patent [19]

Shah

[11] Patent Number: 5,582,978
[45] Date of Patent: Dec. 10, 1996

[54] **NUCLEIC ACID PROBES FOR THE DETECTION OF *HAEMOPHILUS INFLUENZAE***

[75] Inventor: Jyotsna Shah, Nashua, N.H.

[73] Assignee: Amoco Corporation, Chicago, Ill.

[21] Appl. No.: 184,607

[22] Filed: Jan. 21, 1994

[51] Int. Cl.$^6$ ............................. C12Q 1/68; C07H 21/04
[52] U.S. Cl. ...................... 435/6; 536/24.32; 536/24.33; 935/8; 935/77; 935/78
[58] Field of Search ............................. 435/6; 536/24.32, 536/24.33; 935/77, 78

[56] References Cited

U.S. PATENT DOCUMENTS

| | | | |
|---|---|---|---|
| 4,851,330 | 7/1989 | Kohne | 435/6 |
| 5,030,557 | 7/1991 | Hogan et al. | 435/6 |

FOREIGN PATENT DOCUMENTS

| | | |
|---|---|---|
| 0272009 | 6/1988 | European Pat. Off. |
| 9303186 | 2/1993 | WIPO . |

OTHER PUBLICATIONS

Gen–Probe, AccuProbe *Haemophilus influenzae* Culture Identification Test (1992).
Davis et al J. Clin Microb (1991) 29: 2193–2196.
Daly et al J. Clin Micro (1991) 29: 80–82.
Dewhirst et al J. Bacteriol (1992) 174: 2002–2013.
Fox et al., "Comparative Cataloging of 16S Ribosomal Ribonucleic Acid: Molecular Approach to Procaryotic Systematics," International Journal of Systematic Bacteriology 27:44–57, 1977.
Kohne, "Isolation and Characterization of Bacterial Ribosomal RNA Cistrons," Biophysical Journal 8:1104–1118, 1968.
Pace et al., "Homology of Ribosomal Ribonucleic Acid of Diverse Bacterial Species with *Escherichia coli* and *Bacillus stearothermophilus*," 107:543–547, 1971.
Sogin et al., "Phylogenetic Measurement in Procaryotes by Primary Structural Characterization," J. Molec. Evolution 1:173–184, 1972.
Hyypia et al., "Nucleic Acid Probes in the Diagnosis of Human Microbial Pathogens," In: Nucleic Acid Probes, R. H. Symons (ed.), CRC Press, Inc. Boca Raton, FL, 1989, pp. 81–104.
Gutell et al., "Comparative Anatomy of 16–S–like Ribosomal RNA," In: Progress in Nucleic Acid Research and Molecular Biology, Cohn and Moldave (eds.), Academic Press, Inc., 1985, vol. 32, pp. 155–216.
Gutell et al., "A compilation of large subunit RNA sequences presented in a structural format," Nucleic Acids Research 16:r175–r269, 1988.
Davis et al., "Direct Identification of Bacterial Isolates in Blood Cultures by Using a DNA Probe," Journal of Clinical Microbiology 29:2193–2196, 1991.
Taylor et al., "Genome Maps of *Campylobacter jejuni* and *Campylobacter coli*," Journal of Bacteriology 174: 2332–2337, 1992.
Daly et al., "Use of Rapid, Nonradioactive DNA Probes in Culture Confirmation Tests to Detect *Streptococcus agalactiae, Haemophilus influenzae*, and Enterococcus . . . ," Journal of Clinical Microbiology 29:80–82, 1991.
Malouin et al., "DNA Probe Technology for Rapid Detection of *Haemophilus influenzae* in Clinical Specimens," Journal of Clinical Microbiology 26:2132–2138, 1988.
Parsons et al., "DNA Probes for the Identification of *Haemophilus ducreyi*," Journal of Clinical Microbiology 27:1441–1445, 1989.
Holt et al., (eds.), Bergey's Manual of Determinative Bactriology, 9th edition, Williams & Wilkins, Baltimore, p. 195.
Gen–Probe Accuprobe *Haemophilus Influenzae* Culture Identification Test, Gen–Probe Incorporated, pp. 1–4, 1992.

*Primary Examiner*—W. Gary Jones
*Assistant Examiner*—Carla Myers
*Attorney, Agent, or Firm*—Norval B. Galloway

[57] ABSTRACT

Nucleic acids which hybridize to rRNA or rDNA of *Haemophilus influenzae* and methods for using these nucleic acids to detect the presence of *Haemophilus influenzae* in a sample are described.

16 Claims, 2 Drawing Sheets

| Posi-tion: | 171 | 203 | | SEQ ID NO: |
|---|---|---|---|---|
| E. coli | ACGGUAGCUAAUACCGCAUAACGCUCGCAAGACCAAAGAGGGGACCUUCGGGC | | E. coli | 7 |
| A. actyno | ACUGUCGCUAAUACCGCGUAGGGUCGGGNGACGGGAAGUCGCGGGACUUUAUGGC | | A. actyno | 8 |
| H. influT | ACUGUCGCUAAUAUACCGCGUAUUAUCGGAAGAUGAAGUGCGGGACUGAGAGGC | | H. influ | 9 |
| CORE | *** * * | | | |
| P1546 | 3'-ATTTGGCGCATAATAGCCTTCTACTTTCACGCC-5' | | P1546 | 10 |
| H. influA | ACUGUCGCUAAUACCGCGUAGUGUGCGGACGAAAGUGCGGGACUUUNAGGC | | H. influA | |
| P1839 | 3'-TTATGGCGCATCACAGCTCTCTGCTTTCACGCC-5' | | P. 1839 | 11 |
| H. influG | ACUGUCGCUAAUACCGCGUAGUGUCACAGCUCUCUGAGAGACGAAAGGGUGGACUUUUA-NC | | H. influG | |
| P1840 | 3'-TTATGGCGCATCACAGCTCTCTGCTTTCCACC-5' | | P. 1840 | 12 |
| H. aegyp | ACUGUCGCUAAUACCGCGUAGUGUCACAGCUCUCUGAGAGACGAAAGUGCGGGACUGAGAGGC | | H. aegyp | |

| Posi-tion: | 251 | 280 | | |
|---|---|---|---|---|
| E. coli | GAUUAGCUAGUAGGUGGGGUAACGGCUCACCUAGGCGACGAUCCCUAGCUGGU | | E. coli | 13 |
| A. acty4 | GAUUAGCUAGUAGGUGUGGGGUAAGGCCUACCAAGCCGACGAUCGCUAGCUGGU | | A. acty4 | 14 |
| H. aegyp | GAUUAGCUAGUAGGUGGGGUAAAGGCCUACCAAGCCUGCGAUCCUGAGCUGGU | | H. aegyp | 15 |
| H. influ | GAUUAGCUAGUUGGUGGGGUAAAUGCCUACCAAGCCUACGAUCCUGAGCUCUA | | H. influ | 16 |
| P1547 | 3'--CAACCACCCCATTTACGGATGGTTCGGACG-5' | | P. 1547 | |
| CORE | ** * * *** ****** * * * | | | |

FIG. 1

23S rRNA-TARGETED PROBES AND TARGET SEQUENCES

```
Posi-                        291                                          332
tion:                         |                                            |
E. coli   UCAGUGUGUGUUAGUGGAAGCGUCUGGAAAGGCGCGGCGAUACAGGGUGACAGCC    E. coli         17
CORE                                          *
P23HI         3'-CAAUCCUCUUACACAACCCUUCGUGUUAGUUUCUCCCACUAU-5'         P23HI         18
H. influF     AACAGUAU-G-GUUAGGAGAGAAUGUGUUGGAAGCACAAUCAAAGAGGGUGAUNAUC  H. influF     19
H. aegyp      AGCAAUAU-A-GUUAGGAGAGAAUGUGUUGGAAGCACAAUCAAAGAGGGUGAUAAUC  H. aegyp      20
H. pleur      AAUGGUUU-U-GUUAGGAGAGAAUGUGUUGGAAGCACAAUCAAAGAGGGUGAUAAUC  H. pleur      21
H. parain     AAUGACAG-A-GACAGAGGAACAAGCUGGAAGCUGGAAGCUUGGCGACACAGGAUAAGCC H. parain     22
A. actyno     AGCGACAG-A-GACAGAGGAAUGUGCUGGAAGCACCUGGAAGCACAGCGAGACAGGGUGAUAGCC A. actyno Posi-                        338                                          365
tion:                         |                                            |
E. coli   CCCGUACACAAAAAUGCACACAUGCUGUGAGCUCGAUGAG        E. coli             24
CORE         **  **  ** *  *
P1984        3'-CAUAGAUUUUGGUAUAACACCAUGAUU-5'           P1984               25
H. influF    CCCGUAUCUAAAAACCAUAUUGUGGUACUAAGCUAACG      H. influF           26
H. aegyp     CCCGUAUCUAAAAACCAUAUUGUGGUACUAAGCUAACG      H. aegyp            27
H. pleur     CCCGUAUCCGAAAACAUUAUUGGUACUAAGCUAACG        H. pleur            28
H. parain    CCCGUACUCGAAGCUCGUGUUAUGGUACUAAGCUAACG      H. parain
A. actyno    CCUGUUCUUGAAGUCUCGGGUCGUGGUACUAAGCUAACG     A. actyno
```

FIG. 2

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 1:

CCGCACTTTC ATCTTCCGAT AATACGCGGT ATT    33

( 2 ) INFORMATION FOR SEQ ID NO: 2:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 2:

GCAGGCTTGG TAGGCATTTA CCCCACCAAC    30

( 2 ) INFORMATION FOR SEQ ID NO: 3:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CCGCACTTTC GTCTCTCGAC ACTACGCGGT ATT    33

( 2 ) INFORMATION FOR SEQ ID NO: 4:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( x i ) SEQUENCE DESCRIPTION: SEQ ID NO: 4:

CCACCCTTTC GTCTCTCGAC ACTACGCGGT ATT    33

( 2 ) INFORMATION FOR SEQ ID NO: 5:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TTAGTACCAC AATATGGTTT TTAGATAC                                                      28

( 2 ) INFORMATION FOR SEQ ID NO: 6:

( i ) SEQUENCE CHARACTERISTICS:
        ( A ) LENGTH: 42
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TATCACCCTC TTTGATTGTG CTTCCCAACA CATTCTCCTA AC                                       42

( 2 ) INFORMATION FOR SEQ ID NO: 7:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 7:

ACGGUAGCUA AUACCGCAUA ACGUCGCAAG ACCAAAGAGG GGGACCUUCG GGC                           53

( 2 ) INFORMATION FOR SEQ ID NO: 8:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 8:

ACUGUCGCUA AUACCGCGUA GGGUCGGGNG ACGAAAGUGC GGGACUUUAU GGC                           53

( 2 ) INFORMATION FOR SEQ ID NO: 9:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 9:

ACUGUCGCUA AUACCGCGUA UUAUCGGAAG AUGAAAGUGC GGGACUGAGA GGC                           53

( 2 ) INFORMATION FOR SEQ ID NO: 10:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 10:

ACUGUCGCUA AUACCGCGUA GUGUCGAGAG ACGAAAGUGC GGGACUUUNA GGC                           53

( 2 ) INFORMATION FOR SEQ ID NO: 11:

( i ) SEQUENCE CHARACTERISTICS:
        ( A ) LENGTH: 52
        ( B ) TYPE: nucleic acid
        ( C ) STRANDEDNESS: single
        ( D ) TOPOLOGY: linear ( x i ) SEQUENCE DESCRIPTION: SEQ ID NO: 11:

ACUGUCGCUA AUACCGCGUA GUGUCGAGAG ACGAAAGGGU GGGACUUUUA NC                            52

( 2 ) INFORMATION FOR SEQ ID NO: 12:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 12:

ACUGUCGCUA AUACCGCGUA GUGUCGAGAG ACGAAAGUGC GGGACUGAGA GGC      53

( 2 ) INFORMATION FOR SEQ ID NO: 13:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 13:

GAUUAGCUAG UAGGUGGGGU AACGGCUCAC CUAGGCGACG AUCCUAGCU GGU      53

( 2 ) INFORMATION FOR SEQ ID NO: 14:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 14:

GAUUAGGUAG UUGGUGGGGU AAGGGCCUAC CAAGCCGACG AUCGCUAGCU GGU      53

( 2 ) INFORMATION FOR SEQ ID NO: 15:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 15:

GAUUAGGUAG UUGGUGGGGU AAAGGUCUAC CAAGCCUGCG AUCUCUAGCU GGU      53

( 2 ) INFORMATION FOR SEQ ID NO: 16:

( i ) SEQUENCE CHARACTERISTICS:
        ( A ) LENGTH: 53
        ( B ) TYPE: nucleic acid
        ( C ) STRANDEDNESS: single
        ( D ) TOPOLOGY: linear ( x i ) SEQUENCE DESCRIPTION: SEQ ID NO: 16:

GAUUAGGUGC GGGUAGUUGG UGGGGUAAAU GCCUACCAAG CCUGCGAUCU CUA      53

( 2 ) INFORMATION FOR SEQ ID NO: 17:

( i ) SEQUENCE CHARACTERISTICS:
        ( A ) LENGTH: 56
        ( B ) TYPE: nucleic acid
        ( C ) STRANDEDNESS: single
        ( D ) TOPOLOGY: linear ( x i ) SEQUENCE DESCRIPTION: SEQ ID NO: 17:

UCAGUGUGUG UGUUAGUGGA AGCGUCUGGA AAGGCGCGCG AUACAGGGUG ACAGCC      56

( 2 ) INFORMATION FOR SEQ ID NO: 18:

( i ) SEQUENCE CHARACTERISTICS:
        ( A ) LENGTH: 54
        ( B ) TYPE: nucleic acid
        ( C ) STRANDEDNESS: single
        ( D ) TOPOLOGY: linear ( x i ) SEQUENCE DESCRIPTION: SEQ ID NO: 18:

```
AACAGUAUGG  UUAGGAGAAU  GUGUUGGGAA  GCACAAUCAA  AGAGGGUGAU  NAUC         54
```

( 2 ) INFORMATION FOR SEQ ID NO: 19:

( i ) SEQUENCE CHARACTERISTICS:
        ( A ) LENGTH: 54
        ( B ) TYPE: nucleic acid
        ( C ) STRANDEDNESS: single
        ( D ) TOPOLOGY: linear ( x i ) SEQUENCE DESCRIPTION: SEQ ID NO: 19:

```
AGCAAUAUAG  UUAGGAGAAU  GUGUUGGGAA  GCACAAUCAA  AGAGGGUGAU  AAUC         54
```

( 2 ) INFORMATION FOR SEQ ID NO: 20:

( i ) SEQUENCE CHARACTERISTICS:
        ( A ) LENGTH: 54
        ( B ) TYPE: nucleic acid
        ( C ) STRANDEDNESS: single
        ( D ) TOPOLOGY: linear ( x i ) SEQUENCE DESCRIPTION: SEQ ID NO: 20:

```
AAUGGUUUUG  UUAGGAGAAU  GUGCUGGGAA  GCUCAAUCGU  AGAGGGUGAU  AAUC         54
```

( 2 ) INFORMATION FOR SEQ ID NO: 21:

( i ) SEQUENCE CHARACTERISTICS:
        ( A ) LENGTH: 54
        ( B ) TYPE: nucleic acid
        ( C ) STRANDEDNESS: single
        ( D ) TOPOLOGY: linear ( x i ) SEQUENCE DESCRIPTION: SEQ ID NO: 21:

```
AAUGACAGAG  ACAGAGGAAC  AAGCUGGGAA  GCUUGGCGAC  ACAGGGUGAU  AGCC         54
```

( 2 ) INFORMATION FOR SEQ ID NO: 22:

( i ) SEQUENCE CHARACTERISTICS:
        ( A ) LENGTH: 54
        ( B ) TYPE: nucleic acid
        ( C ) STRANDEDNESS: single
        ( D ) TOPOLOGY: linear ( x i ) SEQUENCE DESCRIPTION: SEQ ID NO: 22:

```
AGCGACAGAG  ACAGAGGAAU  GUGCUGGGAA  GCACAGCGAG  ACAGGGUGAU  AGCC         54
```

( 2 ) INFORMATION FOR SEQ ID NO: 23:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( x i ) SEQUENCE DESCRIPTION: SEQ ID NO: 23:

```
CCCGUACACA  AAAAUGCACA  UGCUGUGAGC  UCGAUGAG                            38
```

( 2 ) INFORMATION FOR SEQ ID NO: 24:

( i ) SEQUENCE CHARACTERISTICS:
 ( A ) LENGTH: 38
 ( B ) TYPE: nucleic acid
 ( C ) STRANDEDNESS: single
 ( D ) TOPOLOGY: linear ( x i ) SEQUENCE DESCRIPTION: SEQ ID NO: 24:

CCCGUAUCUA AAAACCAUAU UGUGGUACUA AGCUAACG                    38

( 2 ) INFORMATION FOR SEQ ID NO: 25:

( i ) SEQUENCE CHARACTERISTICS:
  ( A ) LENGTH: 38
  ( B ) TYPE: nucleic acid
  ( C ) STRANDEDNESS: single
  ( D ) TOPOLOGY: linear ( x i ) SEQUENCE DESCRIPTION: SEQ ID NO: 25:

CCCGUAUCUA AAAACCAUAU UGUGGUACUA AGCUAACG                    38

( 2 ) INFORMATION FOR SEQ ID NO: 26:

( i ) SEQUENCE CHARACTERISTICS:
  ( A ) LENGTH: 38
  ( B ) TYPE: nucleic acid
  ( C ) STRANDEDNESS: single
  ( D ) TOPOLOGY: linear ( x i ) SEQUENCE DESCRIPTION: SEQ ID NO: 26:

CCCGUAUCCG AAAACAUUAU UAUGGUACUA AGCUAACG                    38

( 2 ) INFORMATION FOR SEQ ID NO: 27:

( i ) SEQUENCE CHARACTERISTICS:
  ( A ) LENGTH: 38
  ( B ) TYPE: nucleic acid
  ( C ) STRANDEDNESS: single
  ( D ) TOPOLOGY: linear ( x i ) SEQUENCE DESCRIPTION: SEQ ID NO: 27:

CCCGUACUCG AAGUCUGUGU UAUGGUACUA AGCUAACG                    38

( 2 ) INFORMATION FOR SEQ ID NO: 28:

( i ) SEQUENCE CHARACTERISTICS:
  ( A ) LENGTH: 38
  ( B ) TYPE: nucleic acid
  ( C ) STRANDEDNESS: single
  ( D ) TOPOLOGY: linear ( x i ) SEQUENCE DESCRIPTION: SEQ ID NO: 28:

CCUGUUCUUG AAGUCUGGGU CGUGGUACUA AGCUAACG                    38

NUCLEIC ACID PROBES FOR THE DETECTION OF *HAEMOPHILUS INFLUENZAE*

This invention relates to the detection of bacteria belonging to the species *Haemophilus influenzae*.

BACKGROUND OF THE INVENTION

The genus Haemophilus includes bacteria classified as such, for example, in Bergey's *Manual of Systematic Bacteriology* (P. H. A. Sneath, ed., 1984, pp. 558–569, Williams & Wilkins). Haemophilus bacteria are minute to medium sized gram-negative coccobacilli or rods generally less than 1 μm in width and variable in length forming threads or filaments and showing marked polymorphism. They occur as obligate parasites on mucous membranes of man and a variety of animals. Capsules are present in a number of species and are of particular interest in *Haemophilus influenzae*, where they play a part in pathogenesis. The majority of *Haemophilus influenzae* strains can be assigned to any of six biovars (I–VI) on the basis of a few biochemical characteristics, and six serovars (A–F) have been identified on the basis of capsular polysaccharides. In addition, the species *Haemophilus aegyptius* has been shown to be the same species as *Haemophilus influenzae* (Casin et al., Ann. Microbiol. (Paris) 137B:155–163, 1986), and is now considered as another biovar of *H. influenzae* (Bergey's Manual of Determinative Biology, Hoft et al., eds., p. 195, Williams & Wilkins).

*Haemophilus influenzae* type b is a major cause of invasive diseases such as meningitis, epiglottiditis, arthritis, and cellulitis which occur exclusively in infants and children. In the United States, the annual incidence of invasive *Haemophilus influenzae* type b related diseases ranges from 67 to 129 cases per 100,000 children under 5 years of age, and the annual incidence of *Haemophilus meningitis* is 19 to 69 cases per 100,000 children (Broom C. V., Pediatry Infect Dis 779–782, 1987). *Haemophilus influenzae* biovargroup aegyptius is mainly responsible for conjunctivitis, and certain strains are responsible for Brazilian purpuric fever (BPF), a serious invasive disease in children under 10 years of age (Brenner et al., J. Clin. Microbiol. 26:1524–1534, 1988).

The quick and accurate diagnosis of *H. influenzae* is important to treat the various diseases caused by this pathogen. However, most known diagnostic methods are slow or fairly non-specific. Diagnosis of *Haemophilus influenzae* is traditionally performed by microbacterial methods. Usually, Haemophilus colonies appear after overnight incubation on a selective chocolate 7% horse blood agar plate incubated at 37° C. in moistened air supplemented with 7% carbon dioxide. Haemophilus colonies are then speciated and serotyped by biochemical tests for Gram strain morphology, oxidase reaction, hemolytic activity, porphyrin, and the requirement of growth factors X and V. Because of the time-consuming nature of these techniques, a number of rapid serological methods have recently become available. The vast majority are antibody-based tests, but most lack sufficient specificity for conclusive identification of the presence of *Haemophilus influenzae*. Therefore, it is the aim of the present invention to provide nucleic acid probes which allow the specific identification of *Haemophilus influenzae* in a sample in the presence of other bacteria or fungi which are normally present in sampled materials. Such probes may be used in a variety of inexpensive, easy-to-use assay systems which allow an accurate, rapid diagnosis of *Haemophilus influenzae* related diseases, and which avoid many of the disadvantages associated with traditional microbiological techniques.

SUMMARY OF THE INVENTION

In one aspect, the invention features an isolated nucleic acid containing about 10 to 70 nucleotides which forms a stable hybridization duplex under normal hybridization conditions with a region of *Haemophilus influenzae* 16S rRNA or rDNA bounded by nucleotide positions 182 to 193 or 252 to 278 or, alternatively, to a region of *Haemophilus influenzae* 23S rRNA or rDNA bounded by nucleotide positions 343 to 356 (E. coli numbering system). Preferably the nucleic acid is between 20 and 60 nucleotides, and most preferably between 25 and 55 nucleotides in length, and is capable of hybridizing preferentially to rRNA or rDNA of *Haemophilus influenzae* over rRNA or rDNA of non-Haemophilus organisms. Most preferably, the nucleic acid is capable of hybridizing preferentially to rRNA or rDNA of *H. influenzae* over rRNA or rDNA of non-*H. influenzae* organisms.

In preferred embodiments of this aspect of the invention, the nucleic acid forms a stable hybridization duplex under normal hybridization conditions with probe 1546 (SEQ ID NO:1), probe 1984 (SEQ ID NO:5), or a nucleotide sequence which is complementary to either of these probes. Preferably, the nucleic acid contains at least 10, and more preferably at least 20 consecutive nucleotides which are homologous or complementary to probe 1546 (SEQ ID NO:1) or probe 1984 (SEQ ID NO:5). Most preferably, the nucleic acid is 1546 (SEQ ID NO:1) or 1984 (SEQ ID NO:5), or a nucleic acid complementary to one of these probes. In addition, individuals skilled in the art will readily recognize that nucleic acids are subject to modification and alteration, and accordingly, the present invention also includes nucleic acids which are complementary or homologous to at least 90% of any ten, and preferably any 20, consecutive nucleotides within probe 1546 (SEQ ID NO:1) or 1984 (SEQ ID NO:5), and which have the hybridization specificity of these particular probes.

In another aspect, the invention features a set of at least two isolated nucleic acids wherein each nucleic acid is between 10 and 70 nucleotides, and forms a stable hybridization duplex under normal hybridization conditions with a region of *Haemophilus influenzae* 16S rRNA or rDNA bounded by nucleotide positions 182 to 193 or 252 to 278, or a region of *Haemophilus influenzae* 23S rRNA or rDNA bounded by nucleotide positions 305 or 314 or 343 to 356. Preferably each nucleic acid in the set is between 20 and 60 nucleotides, and most preferably between 25 and 55 nucleotides in length. In the event that one of the nucleic acids within the set also forms a stable hybridization duplex with rRNA or rDNA of a non-*Haemophilus influenzae* organism under normal hybridization conditions, a second nucleic acid within the set does not form a stable hybridization duplex with the rRNA or rDNA of the same non-*Haemophilus influenzae* organism under the same hybridization conditions.

In preferred embodiments of this aspect of the invention, the set of nucleic acids includes at least one nucleic acid which is capable of preferentially hybridizing to rRNA or rDNA of *Haemophilus influenzae* over rRNA or rDNA of non-*Haemophilus influenzae* organism. More preferably, at least one of the nucleic acids of the set consists essentially of the nucleotide sequence defined by probe 1546 (SEQ ID NO:1), 1547 (SEQ ID NO:2), 1839 (SEQ ID NO:3), 1840

(SEQ ID NO:4), 1984 (SEQ ID NO:5), 23HI (SEQ ID NO: 6), or a nucleotide sequence complementary to any one of these probes. Especially preferred sets include probes 1546 (SEQ ID NO:1) and 1547 (SEQ ID NO:2); and 1984 (SEQ ID NO: 5) and 23HI (SEQ ID NO:6). In addition, individuals skilled in the art will readily recognize that the sequences of probes 1546 (SEQ ID NO:1), 1547 (SEQ ID NO.: 2), 1839 (SEQ ID NO:3), 1840 (SEQ ID NO:4), 1984 (SEQ ID NO:5), 23HI (SEQ ID NO:6), and their complementary sequences are subject to modifications and alterations. Accordingly, the nucleic acid set of the invention can include one or more nucleic acids which are complementary or homologous to at least 90% of any ten, and preferably any 20, consecutive nucleotides within probe 1546 (SEQ ID NO:1), 1547 (SEQ ID NO: 2), 1839 (SEQ ID NO:3), 1840 (SEQ ID NO:4), 1984 (SEQ ID NO:5) or 23HI (SEQ ID NO:6) and which have the hybridization specificity of these particular probes.

The invention also features a method of detecting the presence of *Haemophilus influenzae* in a sample. The method involves contacting the sample with at least one of the nucleic acids of the invention under normal hybridization conditions which allow the formation of nucleic acid duplexes between the nucleic acid and rRNA or rDNA of *Haemophilus influenzae*, if present, and then monitoring the contacted sample to detect the presence of the nucleic acid duplexes wherein the presence of the duplexes is an indication that *Haemophilus influenzae* is present in the sample. The detection of the duplexes may involve any standard techniques for identifying duplex molecules. Preferably, either the nucleic acid of the invention, or the *Haemophilus influenzae* rRNA or rDNA are labeled with a chemical moiety which is capable of being detected, including without limitation, radioactive isotopes, enzymes, luminescent agents, precipitating agents and dyes.

In one preferred embodiment, the method involves contacting the sample with a set of at least two nucleic acids each of which is capable of hybridizing to the rRNA or rDNA of *Haemophilus influenzae*. Preferred sets of probes include probes 1546 (SEQ ID NO:1) and 1547 (SEQ ID NO:2); and probes 1984 (SEQ ID NO:5) and 23HI (SEQ ID NO:6).

Individuals skilled in the art will readily recognize that the compositions of the present invention can be assembled in a kit for the detection of *Haemophilus influenzae*. Typically, such kits include reagents containing the nucleic acids of the present invention with instructions and suitable packaging for their use as part of an assay for *Haemophilus influenzae*.

The term "isolated nucleic acid," as used herein, refers to a nucleic acid segment or fragment which is not immediately contiguous with (i.e., covalently linked to) both of the nucleic acids with which it is immediately contiguous in the naturally occurring genome of the organism from which the nucleic acid is derived. The term, therefore, includes, for example, a nucleic acid which is incorporated into a vector (e.g., an autonomously replicating virus or plasmid), or a nucleic acid which exists as a separate molecule independent of other nucleic acids such as a nucleic acid fragment produced by chemical means or restriction endonuclease treatment.

A nucleic acid "consisting essentially of" a particular sequence of nucleotides as used herein refers to that particular sequence and other sequences that are identical to the first sequence but for the addition to or removal from the sequence of a few nucleotides (e.g. 2 to 10) which does not prevent the nucleic acid sequence from forming stable hybridization duplex with a particular region of *H. influenzae* rRNA.

"Homologous," as used herein in reference to nucleic acids, refers to the nucleotide sequence similarity between two nucleic acids. When a nucleotide sequence is identical to another sequence, then the two sequences are 100% homologous. The homology between two nucleic acids is a direct function of the number of matching nucleotides at a given position in the sequence, e.g., if half of the positions in the two nucleic acids are the same then they are 50% homologous. Thus, "substantially homologous" means a nucleotide sequence that is not identical to another sequence, but maintains a sufficient sequence identity to retain the same hybridization characteristics as the sequence.

The term "complementary" means that two nucleic acids, e.g. DNA or RNA, contain a series of consecutive nucleotides which are capable of forming base pairs to produce a region of double-strandedness referred to as a hybridization duplex or complex. A duplex forms between nucleic acids because of the orientation of the nucleotides on the RNA or DNA strands; certain bases attract and bond to each other to form a base pair through hydrogen bonding and π-stacking interactions. Thus, adenine in one strand of DNA or RNA pairs with thymine in an opposing complementary DNA strand, or with uracil in an opposing complementary RNA strand. Guanine in one strand of DNA or RNA pairs with cytosine in an opposing complementary strand.

The formation of such hybridization duplexes can be made to be highly specific by adjustment of the conditions (often referred to as stringency) under which this hybridization takes place such that hybridization between two nucleic acids will not form a stable duplex, e.g., a duplex that retains a region of double-strandedness under the predetermined stringency conditions, unless they contain a certain number of nucleotides in specific sequences which are substantially, or completely, complementary. Thus, the phrase "preferentially hybridize" as used herein refers to a nucleic acid which binds to, and forms a stable duplex under normal hybridization conditions with, a second nucleic acid (i.e., *Haemophilus influenzae* rDNA or rRNA), and which does not form a stable duplex with other nucleic acid molecules under the same normal hybridization conditions such as those described herein.

Unless defined otherwise, all technical terms and scientific terms used herein have the same meaning as commonly understood by one of ordinary skill in the art to which this invention belongs. All publications mentioned herein are incorporated by reference. Examples of the preferred methods and materials will now be described. These examples are illustrative only and not intended to be limiting as those skilled in the art will understand that methods and materials similar or equivalent to those described herein can be used in the practice or testing of the present invention.

Other features and advantages of the invention will be apparent from the following detailed description, and from the claims.

DRAWINGS

The drawings will first be briefly described.

FIG. 1 is an illustration of the nucleotide sequences of regions 162 to 214 and 236 to 288 of the 16S RNA from several of the species examined. H. influT=*H. influenzae* type strain; H. influA=*H. influenzae* type A; H. influG=*H. influenzae* type G; H. aegyT=*H. aegyptius* type strain; A. actY4=*A. actinomycemcomitans*. Probes 1546, 1839, 1840, and 1547 are also illustrated. RNA sequences are written 5' to 3'. Probe sequences are written 3'to 5'. The core region is bounded by *.

FIG. 2 is an illustration of the nucleotide sequences of regions 280 to 335 and 335 to 372 of the 23S RNA from several of the species examined. H. influF=*H. influenzae* type strain E; H.; H. aegyT=*H. aegyptius* type strain. H. pleur=*H. pleuropneumo; H. parain=H. parainfluenza* and A. actyno =*A. actinomycetemcomitans*. Probes 23HI and 1984 are also illustrated. RNA sequences are written 5' to 3'. Probe sequences are written 3'to 5'. The core region is bounded by *.

DETAILED DESCRIPTION

Bacterial ribosomes contain three distinct RNA molecules which, at least in *Escherichia coli*, are referred to as 5S, 16S and 23S rRNAs. In eukaryotic organisms, there are four distinct rRNA species, generally referred to as 5S, 18S, 28S, and 5.8S. These names historically are related to the size of the RNA molecules, as determined by their sedimentation rate. In actuality, however, ribosomal RNA molecules vary substantially in size between organisms. Nonetheless, 5S, 16S, and 23S rRNA are commonly used as generic names for the homologous RNA molecules in any bacterium, including Haemophilus, and this convention will be continued herein. The probes of the present invention target specific regions of the 16S and 23S rRNA molecules of the *Haemophilus influenzae*, and are useful to detect this pathogen in biological samples.

I. Identification of Unique Regions of the *Haemophilus influenzae* rRNA genes

The nucleic acid probes of the present invention were developed by comparing regions of *Haemophilus influenzae* rRNA and rDNA to the rRNA and rDNA of close evolutionary relatives based on phylogenetic observations.

As the first step in identifying regions of *Haemophilus influenzae* rRNA which could potentially serve as useful target sites for nucleic acid hybridization probes, complete nucleotide sequences of the 16S rRNAs of *Haemophilus influenzae*, several other species of Haemophilus, and close relatives of Haemophilus were obtained, and partial sequencing of the 23S rRNAs through the "300 Region" (Gutell and Fox, 1988, Nucleic Acid Research, 16 r175–r269) from several serovars of *Haemophilus influenzae*, other species of Haemophilus, and *Actinobacillus actinomycetemcomitans* was performed.

The nucleotide sequences were determined by standard laboratory protocols either by cloning (Maniatis et al., 1982, Molecular Cloning; A Laboratory Manual, Cold Spring Harbor Laboratory, New York, pp 545) and sequencing (Maxam and Gilbert, 1977, *P. N. A. S., USA* 74:560–564; Sanger et al., 1977, P. N. A. S., USA 74:5463–5467) the genes which specify the rRNAs, and/or by direct sequencing of the rRNAs themselves using reverse transcriptase (Lane et al., 1985, *P. N. A. S., USA* 82:6955–6959).

The *Haemophilus influenzae* rRNA nucleotide sequences were then compared to other available rRNA nucleotide sequences, in particular to other species of Haemophilus, and *Actinobacillus actinomycetemcomitans*. The *Escherichia coli* 16S and 23S rRNA sequences are used herein as a convenient standard for identifying particular homologous regions in the Haemophilus rRNAs under consideration.

Comparison of the sequences of different serotypes of *Haemophilus influenzae* and other Haemophilus revealed several regions of sequence which are different in the different serotypes of *Haemophilus influenzae*, and between *Haemophilus influenzae* and non-*Haemophilus influenzae*, and between *Haemophilus influenzae* and non-Haemophilus bacteria (FIGS. 1 and 2).

II. Development of Probes

A minimum of ten nucleotides are necessary in a nucleic acid probe to statistically obtain specificity and for stable hybridization products. Nucleic acids of greater length, up to 2500 nucleotides, have been suggested as probes. However, a maximum of 250 nucleotides presently represents an approximate upper limit for nucleic acid probes in which reaction parameters can be readily adjusted and controlled to determine mismatched sequences and preferential hybridization. The maximum of 250 nucleotides also represents the upper limit of most currently used synthetic methods of generating DNA and RNA molecules. Preferably, useful probes have between 20 and 70 nucleotides. A number of probes were designed to the target regions corresponding variously to complements of the sequences of *Haemophilus influenzae* serovars A, B, and G, or all three.

Oligonucleotide probes, 28–42 nucleotides in length, were designed which hybridize preferentially to *Haemophilus influenzae*. These were designed:

1) to maximally utilize the nucleotide sequence differences useful for distinguishing *Haemophilus influenzae* or Haemophilus from other bacteria, 2) to minimize the effect of self complementarity, both locally within the target rRNA, and between probes, and 3) to contain a "core region" of approximately 10 to 25 nucleotides to maximize specific hybridization to *Haemophilus influenzae* rRNA or rDNA over other species under normal hybridization conditions.

Specifically, the nucleotide sequence of the core region of each probe was designed to have the maximum number of nucleotide mismatches with the rRNA of other species while maintaining sufficient complementarity to allow hybridization of the probe to *Haemophilus influenzae* rRNA. "Nucleotide mismatch" means that a nucleotide position in the probe is occupied by a nucleotide which does not normally form a base pair with the nucleotide at the corresponding position in the complementary target RNA or DNA. The preferred types of mismatches include uracil to uracil, adenine to adenine, guanine to guanine, cytosine to cytosine and thymine to thymine, but adenine to cytosine, uracil to cytosine and thymine to cytosine may also be used.

Single stranded probes were prepared using beta-cyanoethyl phosphoramidite chemistry on a 380-B Synthesizer (Applied Biosystems, Foster City, Calif.). Deprotection of the phosphates and nucleotide bases was accomplished by standard methods and the crude oligonucleotides mixtures were purified by reverse phase HPLC.

This probe selection strategy yielded a number of probes useful for identifying *Haemophilus influenzae* bacteria in samples. Probes 1546 (SEQ ID NO:1), 1547 (SEQ ID NO:2), 1839 (SEQ ID NO:3) and 1840 (SEQ ID NO:4) are designed from 16S rRNA sequences, and probes 1984 (SEQ ID NO: 5) and 23HI (SEQ ID NO:6) are designed from 23S rRNA sequences. The probe sequences are set forth below.

16S rRNA-Targeted Probes:

Probe 1546:  5'-CCGCACTTTCATCTTCCGATAATACGCGGTATT-3'  (SEQ ID NO: 1)
Probe 1547:  5'-GCAGGCTTGGTAGGCATTTACCCCACCAAC-3'  (SEQ ID NO: 2)
Probe 1839:  5'-CCGCACTTTCGTCTCTCGACACTACGCGGTATT-3'  (SEQ ID NO: 3)
Probe 1840:  5'-CCACCCTTTCGTCTCTCGACACTACGCGGTATT-3'  (SEQ ID NO: 4)

23s rRNA-Targeted Probes:

Probe 1984:  5'-TTAGTACCACAATATGGTTTTTAGATAC-3'  (SEQ ID NO: 5)
Probe 23HI:  5'-CAATCCTCTTACACAACCCTTCGTGTTAGTTTCTCCCACTAT-3'  (SEQ ID NO: 6)

III. Hybridization Conditions

In general, hybridization conditions are defined by the base composition of the nucleic acid duplex, as well as by the level and geometry of mispairing between the two nucleic acids. Reaction parameters which are commonly adjusted include concentration and type of ionic species present in the hybridization solution, the types and concentrations of denaturing agents present, and the temperature of hybridization. Generally, as hybridization conditions become more stringent, longer probes are preferred if stable hybrids are to be formed. As a corollary, the stringency of the conditions under which hybridization is to take place (e.g., based on the type of assay to be performed) will dictate certain characteristics of the preferred probes to be employed. Such relationships are well understood and can be readily manipulated by those skilled in the art (see for example, Ausebel et al. *Current Protocols in Molecular Biology*, John Wiley & sons, New York, 1989). For example, the appropriate hybridization conditions for any particular probe may be determined using the melting temperature ($T_m$) of the desired duplex molecule as a guide. The $T_m$ of any DNA-DNA duplex may be approximated from the equation of Mein Koth and Wahl:

$$T_m = 81.5°\ C. + 16.6(\log M) + 0.41(\%\ GC) - 0.61(\%\ \text{form}) - 500/2$$

and for RNA-DNA hybrids from the equation of Casey and Davidson:

$$T_m = 79.8°\ C. + 18.5(\log M) + 0.58(\%\ GC) - 11.8(\%\ GC)^2 - 0.56(\%\ \text{form}) - 820/2$$

where M is the molarity of monovalent cations, % GC is the percentage of guanosine and cytosine nucleotides in the DNA, % form is the percentage of formamide in the hybridization solution, an L is the length of the hybrid duplex in base pairs.

Generally, for the specific probes disclosed, normal hybridization conditions involve hybridization in a high salt solution that promotes base-pairing between the probe and target sequence at a temperature between 42° C. and 68° C. As is well known, the specificity of the particular probe is defined by the post-hybridization washes, which in the present case are typically carried out at 60° C.–68° C. at an ionic concentration which is ten to thirty times lower than the concentration used in the hybridization step.

The specific hybridization behaviors of the nucleic acid probes described above are dependent to a significant extent on the assay format in which they are employed. Conversely, the assay format will dictate certain optimal design features of particular nucleic acids. For example, the length of the particular oligonucleotides described herein was optimized for use in the dot blot assay but may be used in other standard hybridization assays. It is well known to one skilled in the art that optimal probe length will be a function of the stringency of the hybridization conditions chosen; hence the length of the instant probes may be altered in accordance with these conditions as long as the probe includes a sequence substantially homologous or complementary to the "core regions" defined herein. Also, in considering sets comprised of more than one nucleic acid probe, it is desirable that all probes behave in a compatible manner in any particular format in which they are both employed. Thus, the exact length of a particular nucleic acid probe will, to a certain extent, reflect its specific intended use.

IV. Hybridization Analysis of Probe Behavior

The sequence comparison suggested that the nucleic acid probes of the present invention should exhibit a variety of useful hybridization properties with respect to the specific detection of *Haemophilus influenzae* or other Haemophilus species, or both, to the exclusion of other bacteria. Equally as important as the inclusivity behavior of the probes is their exclusivity behavior, i.e., their reactivity toward non-Haemophilus bacteria.

The behavior of the probes toward representative *Haemophilus influenzae* and non-Haemophilus bacteria was determined by hybridization analysis using a dot blot procedure. While hybridization data for each of the individual probes of the present invention are provided (Tables 1 and 2), it should be noted that useful combinations (sets) of probes which exhibit hybridization behaviors that are the sum of the individual probes also is explicitly predicted by the data.

EXAMPLE 1

Dot Blot Analysis Of Probe Hybridization Behavior

Dot blot analysis, in accordance with well known procedures, involves immobilizing a target rRNA or rDNA or a population of target nucleic acids on a filter such as a nitrocellulose, nylon, or other derivatized membrane which readily can be obtained commercially, specifically for this purpose. Either DNA or RNA can be easily immobilized on such a filter and subsequently tested for hybridization under any of a variety of conditions (i.e., stringencies) with the nucleic acid probes of the invention. Under controlled conditions, probes whose nucleotide sequences have greater complementarity to the target sequence will exhibit a higher level of hybridization than probes having less complementarity.

One tenth of a microgram of purified RNA (Lane et al., 1985, *P. N. A. S., USA* 82:6955–6959), or cells from each of the indicated organisms, was spotted on nitrocellulose filters. The oligonucleotide probes were end-labeled with radioactive phosphorous 32 using standard procedures.

Hybridization to the rRNA targets at 60° C. for 14–16 hours (in a hybridization solution containing 0.9M NaCl, 0.12M Tris-HCl, pH 7.8, 6 mM EDTA, 0.1M KP0$_4$, 0.1% SDS, 0.1% pyrophosphate, 0.002% ficoll, 0.02% BSA, and 0.002% polyvinylpyrrolidine), followed by three 15 minute post-hybridization washes at 60° C (in 0.03M NaCl, 0.004M Tris-HCl, pH 7.8, 0.2 mM EDTA, and 0.1% SDS) to remove unbound probes, was found to be sufficiently stringent to produce a high level of probe specificity.

Following hybridization and washing as described above, the hybridization filters were exposed to x-ray film overnight with two intensifying screens, and the intensity of the signal was scored visually with respect to control spots of known amount of target material (RNA). A signal of four positive signs (++++) indicates a high level of hybridization, and this level was used as a standard. In comparison to this standard or control level, two positive signs (++) indicates a faint level of hybridization, one positive sign (+) a level that is barely detectable, and a negative (−) sign indicates that hybridization was undetectable.

Table 1 exemplifies the inclusivity behavior of the preferred probes toward a representative sampling of the different serotypes of *Haemophilus influenzae* as well as from the biovar aegyptius in a dot blot hybridization assay. Either purified RNA or cells were tested. As used in Table 1, "Cyto-dots" are cells lysed onto nitrocellulose by standard NaOH treatment, followed by neutralization with Tris buffer pH 7.4.

TABLE 1

| | Target: Probe: | 16S | | | | 23S |
|---|---|---|---|---|---|---|
| Genus, species | strain | 1546 | 1547 | 1839 | 1840 | 1984 |
| RNA | | | | | | |
| *Haemophilus influenza* | GT0244 | ++++ | ++++ | +++ | ++++ | ++++ |
| *Haemophilus influenza* A | GT2563 | − | ++++ | ++++ | +++ | ++++ |
| *Haemophilus influenza* B | GT2564 | ++++ | ++++ | − | + | ++++ |
| *Haemophilus influenza* B | GT2565 | ++++ | ++++ | − | + | ++++ |
| *Haemophilus influenza* C | GT2566 | ++++ | ++++ | ++++ | +++ | ++++ |
| *Haemophilus influenza* D | GT2567 | ++++ | ++++ | − | + | ++++ |
| *Haemophilus influenza* E | GT2568 | ++++ | ++++ | +++ | +++ | ++++ |
| *Haemophilus influenza* F | GT2569 | − | ++++ | ++++ | ++++ | ++++ |
| *Haemophilus influenza* | ATCC33391 | ++++ | ++++ | ++++ | ++++ | ++++ |
| *Haemophilus aegyptius* | NCTC8052 | − | ++++ | ++++ | ++++ | ++++ |
| Cyto-dots | | | | | | |
| *Haemophilus influenza* | GT0244 | ++++ | ++++ | ++ | ++++ | ++++ |
| *Haemophilus influenza* A | GT2563 | − | ++++ | + | ++ | ++++ |
| *Haemophilus influenza* B | GT2564 | ++++ | ++++ | − | + | ++++ |
| *Haemophilus influenza* B | GT2565 | ++++ | ++++ | − | + | ++++ |
| *Haemophilus influenza* C | GT2566 | ++++ | ++++ | ++++ | ++++ | ++++ |
| *Haemophilus influenza* D | GT2567 | ++++ | ++++ | − | + | ++++ |
| *Haemophilus influenza* E | GT2568 | ++++ | ++++ | + | ++ | ++++ |
| *Haemophilus influenza* F | GT2569 | − | ++++ | + | ++++ | ++++ |
| *Haemophilus influenza* | GT1367 | − | ++++ | + | ++ | ++++ |
| *Haemophilus influenza* | GT1372 | − | ++++ | + | ++++ | ++++ |
| *Haemophilus influenza* | GT1680 | ++++ | ++++ | − | + | ++++ |
| *Haemophilus influenza* | GT1861 | ++++ | ++++ | + | ++++ | ++++ |
| *Haemophilus influenza* | GT1862 | ++++ | ++++ | − | + | ++++ |
| *Haemophilus influenza* | GT1882 | ++++ | ++++ | − | + | ++++ |
| *Haemophilus influenza* | GT1883 | ++++ | ++++ | − | + | ++++ |
| *Haemophilus influenza* | GT1884 | ++++ | ++++ | − | + | ++++ |
| *Haemophilus influenza* | GT1885 | ++++ | ++++ | − | + | ++++ |
| *Haemophilus influenza* | GT1886 | ++++ | ++++ | − | + | ++++ |
| *Haemophilus influenza* | GT1948 | ++++ | ++++ | − | + | ++++ |
| *Haemophilus influenza* | GT1949 | ++++ | ++++ | − | + | ++++ |
| *Haemophilus influenza* | GT1950 | ++++ | ++++ | − | + | ++++ |
| *Haemophilus influenza* | GT1951 | ++++ | ++++ | +++ | ++++ | ++++ |
| *Haemophilus influenza* | GT1973 | ++++ | ++++ | − | + | ++++ |
| *Haemophilus influenza* | GT2016 | ++++ | ++++ | − | + | ++++ |
| *Haemophilus influenza* | GT2017 | − | ++++ | ++++ | ++++ | ++++ |
| *Haemophilus influenza* | GT2058 | ++++ | ++++ | − | + | ++++ |
| *Haemophilus influenza* | GT2059 | ++++ | ++++ | − | + | ++++ |
| *Haemophilus influenza* | GT2130 | nd | ++++ | − | + | ++++ |
| *Haemophilus influenza* | GT2156 | − | ++++ | − | − | ++++ |

100 ng RNA or 5 ul of cells (10E10) were spotted per dot.
Results were recorded after overnight exposure of autoradiographs with 2 intensifying screens.
nd = not done
++++ = control level of hybridization;
+ = barely visible; and
− = zero Table 2 exemplifies the exclusivity behavior of the preferred probes toward a representative sampling of non-Haemophilus bacteria in a dot blot hybridization assay.

TABLE 2

DOT-BLOT HYBRIDIZATION OF 16S AND 23S rRNA-TARGETED PROBES
(EXCLUSIVITY TESTING)

| Genus, species | Target: Probe: strain | 16S | | | | 23S |
|---|---|---|---|---|---|---|
| | | 1546 | 1547 | 1839 | 1840 | 1984 |
| RNA | | | | | | |
| Haemophilus influenza | ATCC33391 | ++++ | ++++ | ++++ | +++ | ++++ |
| Haemophilus aphrophilus | ATCC33389 | +/− | ++++ | + | ++ | − |
| Haemophilus aviam | NCTC11297 | − | ++++ | − | + | − |
| Haemophilus ducreyii | GT0243 | − | − | − | − | − |
| Haemophilus haemoglobin | NCTC1659 | − | − | − | + | − |
| Haemophilus parainfluenza | ATCC29241 | − | − | − | + | − |
| Haemophilus parainfluenza | GT1368 | − | − | − | − | − |
| Haemophilus parainfluenza | GT2131 | − | ++++ | − | + | − |
| Haemophilus parainfluenza | GT2193 | − | − | − | − | − |
| Haemophilus pleuropneumo. | ATCC27088 | − | − | − | + | − |
| Haemophilus segnis | ATCC33393 | − | +++ | ++++ | +++ | − |
| A. actinomycetemcomitans | GT0004 | − | +++ | ++++ | ++ | − |
| A. actinomycetemcomitans | ATCC29522 | − | +++ | ++++ | ++ | − |
| A. actinomycetemcomitans | ATCC29524 | − | ++++ | ++++ | ++ | − |
| A. actinomycetemcomitans | ATCC29523 | − | ++++ | ++++ | ++ | − |
| A. seminis | ATCC15768 | − | ++++ | − | ++++ | − |
| A. equuli | NCTC08829 | − | +++ | − | + | − |
| A. ligieresii | ATCC19393 | − | − | − | + | − |
| A. suis | ATCC15557 | − | +++ | − | + | − |
| Acholeplasma lalawii | ATCC32063 | − | − | − | + | − |
| Actinomyces israelii | ATCC10049 | nd | nd | nd | nd | − |
| Actinomyces odontolyticulus | ATCC17929 | nd | nd | nd | nd | − |
| Agrobacterium tumefaciens | ATCC15955 | nd | nd | nd | nd | − |
| Arthrobacter globiformis | ATCC08010 | nd | nd | nd | nd | − |
| Bacillus subtilis | ATCC23059 | nd | nd | nd | nd | − |
| Bacteroides fragilis | ATCC25285 | nd | nd | nd | nd | − |
| Bifidobacterium dentium | ATCC27534 | nd | nd | nd | nd | − |
| Bordetella pertussis | ATCC08467 | nd | nd | nd | nd | − |
| Chlorobium limicola | | nd | nd | nd | nd | − |
| Chloroflexus aurantiacus | Y400 | nd | nd | nd | nd | − |
| Citrobacter freundii | ATCC08090 | nd | nd | nd | nd | − |
| Campylobacter jejuni | ATCC33560 | nd | nd | nd | nd | − |
| Clostridium clostridioforme | ATCC25537 | nd | nd | nd | nd | − |
| Corynebacterium genitalium | ATCC33031 | nd | nd | nd | nd | − |
| Corynebacterium glutamicum | ATCC13032 | nd | nd | nd | nd | − |
| Corynebacterium pseudodiphtheriticum | DSM2097 | nd | nd | nd | nd | − |
| Corynebacterium pseudotuberculosis | ATCC19410 | nd | nd | nd | nd | − |
| Corynebacterium pyogenes | ATCC19411 | nd | nd | nd | nd | − |
| Corynebacterium xerosis | ATCC00373 | nd | nd | nd | nd | − |
| Corynebacterium diphtheriae | ATCC11913 | nd | nd | nd | nd | − |
| Corynebacterium diphtheriae | ATCC13812 | nd | nd | nd | nd | − |
| Desulfovibrio desulfuricans | ATCC07757 | − | − | − | − | − |
| Deinococcus radiodurans | ATCC35073 | nd | nd | nd | nd | − |
| Erwinia | GT1751 | nd | nd | nd | nd | − |
| Escherichia coli | N99 | − | − | − | − | − |
| Escherichia coli | GT1665 | − | − | − | + | − |
| Fusobacterium necrophorum | ATCC00238 | nd | nd | nd | nd | − |
| Jonesia denitrificans | GT0666 | nd | nd | nd | nd | − |
| K. rhinoscleromitis | GT1881 | nd | nd | nd | nd | − |
| Klebsiella pneumoniae | ATCC13883 | nd | nd | nd | nd | − |
| Micrococcus conoglomeratus | ATCC00401 | nd | nd | nd | nd | − |
| Micrococcus luteus | ATCC00381 | nd | nd | nd | nd | − |
| Mycobacterium species | GT0298 | nd | nd | nd | nd | − |
| Mycoplasma pneumonia | ATCC15531 | − | − | − | + | − |
| Mycoplasma putrefaciens | ATCC15718 | − | − | − | + | − |
| Mycoplasma genitalium | ATCC33530 | − | − | − | + | − |
| Mycoplasma hominis | ATCC23114 | − | − | − | + | − |
| Nocardia asteroides | ATCC03308 | nd | nd | nd | nd | − |
| Nocardia albus | DSM43109 | nd | nd | nd | nd | − |
| Nocardia dassonvillei | DSM43235 | nd | nd | nd | nd | − |
| Pimelobacter simplex | DSM08929 | nd | nd | nd | nd | − |
| Pasteurella aerogenes | ATCC27883 | − | ++++ | − | + | − |
| Pasteurella gallinarum | NCTC11188 | − | ++++ | − | + | − |
| Pasteurella multocida | ATCC10322 | − | ++++ | − | + | − |
| Pasteurella ureae | IngarOslen | − | ++++ | − | + | − |

TABLE 2-continued

DOT-BLOT HYBRIDIZATION OF 16S AND 23S rRNA-TARGETED PROBES
(EXCLUSIVITY TESTING)

| Genus, species | Target: Probe: strain | 16S | | | | 23S |
|---|---|---|---|---|---|---|
| | | 1546 | 1547 | 1839 | 1840 | 1984 |
| *Propionobacterium acnes* | ATCC06919 | nd | nd | nd | nd | – |
| *Propionobacterium thoenii* | DMS20276 | nd | nd | nd | nd | – |
| *Psedomonas cepacia* | ATCC13945 | – | – | – | + | – |
| *Rhodococcus aurantiacus* | GT3589 | nd | nd | nd | nd | – |
| *Rhodococcus bronchialis* | ATCC25592 | nd | nd | nd | nd | – |
| *Rhodococcus equi* | GT0665 | nd | nd | nd | nd | – |
| *Rhodococcus erythopolis* | ATCC19369 | nd | nd | nd | nd | – |
| *Rhodococcus fascians* | ATCC12974 | nd | nd | nd | nd | – |
| *Rhodococcus ketoglutanicum* | ATCC15587 | nd | nd | nd | nd | – |
| *Rhodococcus obuensis* | ATCC33610 | nd | nd | nd | nd | – |
| *Rhodococcus rhodochrous* | ATCC04273 | nd | nd | nd | nd | – |
| *Rhodococcus sputi* | ATCC29627 | nd | nd | nd | nd | – |
| *Salmonella typhimurium* | e23566 | nd | nd | nd | nd | – |
| *Spirochaeta aurantia* | | nd | nd | nd | nd | – |
| *Staphylococcus aureus* | ATCC12600 | nd | nd | nd | nd | – |
| *Staphylococcus aureus* | GT1711 | – | – | – | + | – |
| *Streptomyces griseus* | ATCC10137 | nd | nd | nd | nd | – |
| *Streptococcus faecalis* | ATCC19433 | nd | nd | nd | nd | – |
| *Streptomyces mutans* | GT0409 | nd | nd | nd | nd | – |
| *Streptomyces mitis* | GT3490 | nd | nd | nd | nd | – |
| *Candida albicans* | 1008–88 | – | – | – | + | – |
| *Crytococcus neoformans* | | nd | nd | nd | nd | – |
| Human Blood | | – | – | – | + | – |
| Human T-cells | | nd | nd | nd | nd | – |
| Mouse L-Cell | | – | – | – | + | – |
| Normal stool | | nd | nd | nd | nd | – |
| Wheat Germ | | nd | nd | nd | nd | – |

100 ng RNA spotted per dot
Results were recorded after overnight exposure of autoradiographs with 2 intensifying screens
++++ = control level of hybridization;
+ = barely visible; and
– = zero.
A. = Actinobacillus
nd = not done These data demonstrate that for the probes derived from the 16S rRNA sequence, Probe 1546 hybridizes specifically to *Haemophilus influenza* types B, C, D and E and not to any of the other strains tested. Probe 1547 hybridizes to all *Haemophilus influenza* bacteria as well as to some other species of Haemophilus (*Haemophilus aphrophilus, Haemophilus avium*, a few Haemophilus parainfluenza isolates, and *Haemophilus segnis*). It also hybridizes to bacteria other than genus Haemophilus (*A. actinomycetemcomitans, A. seminis, A. equli, A. suis*, and Pasteurella species). Probe 1839 hybridizes to *Haemophilus influenza* types A, C, E, F, and *A. actinomycetemcomitans*.

In addition, these data demonstrate that for the probes derived from the 23S rRNA sequence, probe 1984 is highly specific and exclusive for serotypes A, B, C, D, E, and F and *Haemophilus aegyptius*. In contrast, Probe 23H1 was designed as a probe for the general detection of 23S rRNA in a sample.

EXAMPLE 2

Dual Probe Liquid-Hybridization Assay

The probes of the present invention or derivatives thereof are of significant value in a variety of hybridization formats. One such format, a dual probe, sandwich-type hybridization assay format (e.g., the homopolymer capture, dual probe, liquid hybridization format described in U.S. Pat. No. 5,147,778, which is incorporated herein by reference), is used in this example. In general, in such an application, an oligonucleotide probe is modified at its 3' terminus to contain a tract of deoxyadenosine (dA) residues ca. 20–200 residues long. This would be used to "capture" the target rRNA (following liquid hybridization) from the test sample onto a solid support (e.g., beads, plastic surface, filter, etc.) which had been suitably derivatized with poly-deoxythymidine (dT) for this purpose. A second probe is used as a detection probe and would be derivatized with a label (e.g. $^{32}$p, fluorescein, biotin, etc.). In principle, the detection probe could be an oligonucleotide or a longer DNA or RNA probe. Preferably, each probe binds to contiguous areas of the target. Detection of the presence of the target nucleic acid in a test sample then is indicated by the capture of the detection probe onto the solid surface.

This could occur only if the target nucleic acid is present in the test sample. Examples of preferred capture probes are 1546 (SEQ ID NO:1) and 1984 (SEQ ID NO:5). Preferred detector probes are 1547 and 23HI. Preferably, probe 1546 (SEQ ID NO:1) is used with probe 1547 (SEQ ID NO:2) and probe 1984 (SEQ ID NO:5) is used with probe 23HI (SEQ ID NO:6).

Other Embodiments

While the description of the invention has been made with reference to detecting rRNA of *Haemophilus influenzae*, it will be readily understood that the probes described herein and probes complementary to those described herein will also be useful for, 1) PCR amplification of ribosomal genes;
2) the detection of the genes (DNA) which specify the rRNA and, accordingly, such probes are to be deemed equivalents to the described probes and encompassed within the spirit and scope to the present invention and the appended claims; and,
3) incorporation into MDV-1 like rRNA which can be amplified by the enzyme Q-Beta replicase.

Thus, while preferred embodiments have been illustrated and described, it is understood that the present invention is capable of variation and modification and, therefore, should not be limited to the precise details set forth, but should include such changes and alterations that fall within the purview of the following claims.

What is claimed is:

1. An isolated nucleic acid consisting of a sequence of nucleotides that is fully complementary or identical to any one of probes 1546 (SEQ ID NO:1), 1547 (SEQ ID NO:2), 1839 (SEQ ID NO:3), or 1840 (SEQ ID NO:4).

2. An isolated nucleic acid of claim 1, consisting of a sequence of nucleotides that is fully complementary or identical to probe 1546 (SEQ ID NO:1).

3. An isolated nucleic acid of claim 1, consisting of a sequence of nucleotides that is fully complementary or identical to probe 1547 (SEQ ID NO:2).

4. An isolated nucleic acid of claim 1, consisting of a sequence of nucleotides that is fully complementary or identical to probe 1839 (SEQ ID NO:3).

5. An isolated nucleic acid of claim 1, consisting of a sequence of nucleotides that is fully complementary or identical to probe 1840 (SEQ ID NO:4).

6. A set of at least two different isolated nucleic acids, wherein a first of said nucleic acids consists of a sequence of nucleotides that is fully complementary or identical to any one of probes 1546 (SEQ ID NO:1), 1839 (SEQ ID NO:3), or 1840 (SEQ ID NO:4), and a second nucleic acid consists of a nucleic acid of claim 3.

7. A set of nucleic acids of claim 6, wherein said first nucleic acid consists of a sequence of nucleotides that is fully complementary or identical to probe 1546 (SEQ ID NO:1).

8. A method of detecting the presence of *Haemophilus influenzas* in a sample comprising:

a) contacting the sample with at least one nucleic acid of claim 2;

b) imposing normal hybridization conditions on the sample and said nucleic acid which allow the formation of a hybridization duplex between said nucleic acid and 1 6S rRNA or rDNA of *Haemophilus influenzue*, if present in the sample, and do not allow said nucleic acid to form a stable nucleic acid duplex with non-*Haemophilus influenzas* organisms; and c) monitoring the sample contacted with said nucleic acid to detect said duplex, the presence of said duplex indicating the presence of *Haemophilus influenzas* in the sample.

9. A kit for detecting the presence of *Haemophilus influenzas* comprising a nucleic acid of claim 1.

10. An isolated nucleic acid consisting of a sequence of nucleotides that is fully complementary or identical to probe 1984 (SEQ ID NO:5).

11. An isolated nucleic acid consisting of a sequence of nucleotides that is fully complementary or identical to probe 23HI (SEQ ID NO:6).

12. A set of at least two different isolated nucleic acids, wherein a first of said nucleic acids consists of a nucleic acid of claim 10, and a second nucleic acid consists of a sequence of nucleotides that is fully complementary or identical to probe 23HI (SEQ ID NO:6).

13. A method of detecting the presence of *Haemophilus influenzas* in a sample comprising:

a) contacting the sample with at least one nucleic acid of claim 10;

b) imposing normal hybridization conditions on the sample and said nucleic acid which allow the formation of a hybridization duplex between said nucleic acid and 23S rRNA or rDNA of *Haemophilus influenzas*, if present in the sample, and do not allow said nucleic acid to form a stable nucleic acid duplex with non-*Haemophilus influenzas* organisms; and c) monitoring the sample contacted with said nucleic acid to detect said duplex, the presence of said duplex indicating the presence of *Haemophilus influenzas* in the sample.

14. A kit for detecting the presence of *Haemophilus influenzas* comprising a nucleic acid of claim 10.

15. A probe consisting of an isolated nucleic acid of claim 1, and one or more of a label, a homopolymeric nucleotide sequence of 20 to 200 nucleotides, or an MDV-1 like nucleic acid that can be amplified by Q-beta replicase.

16. A probe consisting of an isolated nucleic acid of claim 10, and one or more of a label, a homopolymeric nucleotide sequence of 20 to 200 nucleotides, or an MDV-1 like nucleic acid that can be amplified by Q-beta replicase.

* * * * *